(12) United States Patent
Aerts et al.

(10) Patent No.: US 8,410,081 B2
(45) Date of Patent: Apr. 2, 2013

(54) TREATMENT OF CYSTIC FIBROSIS

(75) Inventors: Johannes Maria Franciscus Gerardus Aerts, Abcoude (NL); Rolf Gabriel Boot, Amsterdam (NL)

(73) Assignee: Academisch Medisch Centrum, Amsterdam (NL)

( * ) Notice: Subject to any disclaimer, the term of this patent is extended or adjusted under 35 U.S.C. 154(b) by 872 days.

(21) Appl. No.: 12/298,506

(22) PCT Filed: Apr. 24, 2007

(86) PCT No.: PCT/NL2007/050177
§ 371 (c)(1),
(2), (4) Date: Mar. 2, 2009

(87) PCT Pub. No.: WO2007/123403
PCT Pub. Date: Nov. 1, 2007

(65) Prior Publication Data
US 2009/0186862 A1    Jul. 23, 2009

Related U.S. Application Data

(60) Provisional application No. 60/794,088, filed on Apr. 24, 2006.

(51) Int. Cl.
*A01N 45/00* (2006.01)
*A61K 31/56* (2006.01)

(52) U.S. Cl. .................................. 514/169; 514/176

(58) Field of Classification Search .................... None
See application file for complete search history.

(56) References Cited

U.S. PATENT DOCUMENTS 7,973,054 B2 * 7/2011 Becq et al. ............... 514/315

FOREIGN PATENT DOCUMENTS

| WO | 9802161 A1 | 1/1998 |
|---|---|---|
| WO | 0102586 A1 | 1/2001 |
| WO | WO 2005046672 | * 3/2005 |
| WO | 2005046672 A1 | 5/2005 |
| WO | 2005123055 A1 | 12/2005 |
| WO | 2007014327 A2 | 2/2007 |

OTHER PUBLICATIONS

Norez et al: "Rescue of functional del F508-CFTR channel s in cystic fibrosis epithelial cells by the alpha-glucosidase inhibitor miglustat". Apr. 3, 2006, pp. 2081-2086, vol. 580, No. 8, Elsevier, Amsterdam, NL.
Gold V et al: "IUPAC Compendium of Chemical Terminology, 2nd Edition" Compendium of Chemical Terminology. International Union of Pure & Applied Chemistry (IUPAC ) Recommendations,1997, p. 1349, Oxford, Blackwell Scientific, GB.
Overkleeft H S et al: "Generation of Specific Deoxynojirimycin-Type Inhibitors of the Non-Lysosomal Glucosylceramidase" Journal of Biological Chemistry, vol. 273, No. 41, Oct. 9, 1998, pp. 26522-26527, Birmingham, US.
Matern H et al: "Purifcation and characerization of a microsomal bile acid beta-glucosidase from human liver." The Journal of Biological Chemistry, vol . 272, No. 17, Apr. 25, 1997, pp. 11261-11267.
Boot Rolf G et al: "Identification of the 1-10 non-lysosomal glucosylceramidase as beta-glucosidase 2. " The Journal of Biological Chemistry, vol. 282, No. 2, Jan. 12, 2007, pp. 1305-1312.

* cited by examiner

*Primary Examiner* — Brian Gulledge
*Assistant Examiner* — Snigdha Maewall
(74) *Attorney, Agent, or Firm* — Browdy and Neimark, PLLC

(57) ABSTRACT

The present invention discloses a therapeutic target for the treatment of cystic fibrosis. It was found that inhibition of non-lysosomal glucosylceramidase (GBA2) sufficiently restores chloride current in cells from CF patients carrying the common delF508-CFTR mutation. With the catalytic center (4) of the enzyme positioned on top of the membrane bilayer face particularly potent inhibitors are found in deoxynojirimycin derivatives having a group that is capable of inserting in the membrane bilayer.

11 Claims, 1 Drawing Sheet

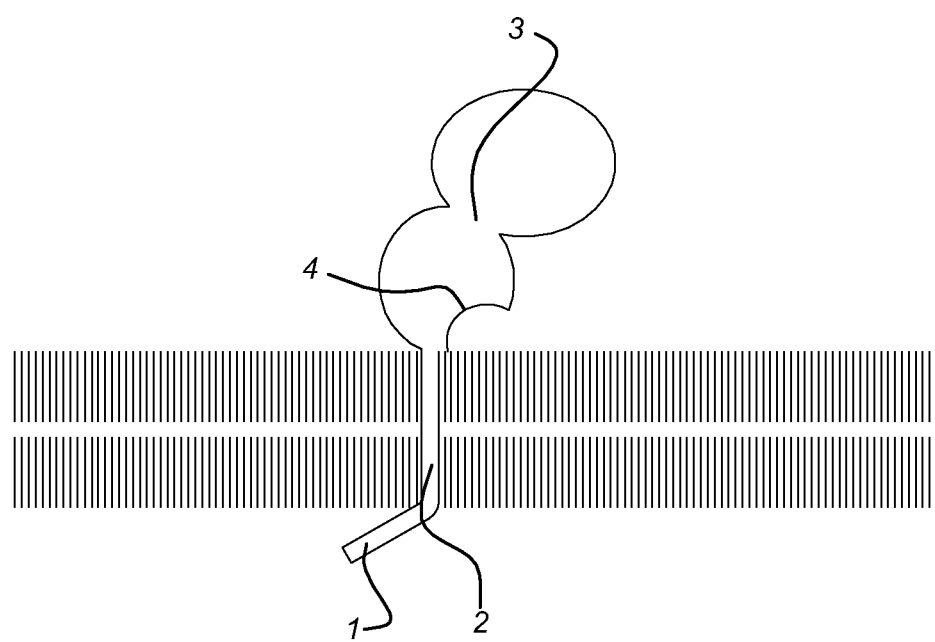

TREATMENT OF CYSTIC FIBROSIS

FIELD OF THE INVENTION

The present invention is in the field of cystic fibrosis. In particular a therapeutic target and suitable compounds for treatment of cystic fibrosis are provided.

BACKGROUND OF THE INVENTION

Cystic fibrosis (CF) is an inherited condition that affects various parts of the body, particularly the lungs and digestive system. CF is the most common inherited disease in white people, affecting about 1 in every 2,500 children born. About one in five babies with CF are diagnosed at birth, when their gut becomes blocked by extra thick meconium. This condition may need surgery. Just over half of people with CF are diagnosed as babies because they are not growing or putting on weight as they should. This is because the pancreas is not producing sufficient lipolytic enzymes resulting in suboptimal assimilation of fat in food resulting in reduced caloric uptake and growth retardation. Untreated CF patients continue to have oily bowel movements, abdominal pain, and problems putting on weight. Constipation is also a frequent symptom. Occasionally the gut becomes completely blocked, resulting in extreme stomach pain.

CF is also characterized by lung involvement. In a healthy person, there is a constant flow of mucus over the surfaces of the air passages in the lungs which removes debris and bacteria. In CF, the mucus is excessively sticky and provides an ideal environment for bacterial growth. Patients with CF are at risk of bacterial chest infections and pneumonia. If they are not treated early and properly, these are very difficult to cure. Symptoms include persistent coughing, excess production of sputum (saliva and mucus), wheezing, and shortness of breath with ordinary activities. Other problems associated with CF have been identified.

CF is recessively inherited, the affected (CFTR) gene is located on chromosome number 7. The gene encodes the chloride channel CFTR. In cystic fibrosis (CF), the most common mutation delF508 which results in reduced activity and cell surface expression of the CF gene protein, the chloride channel CFTR. About 1 in 22 of the white population in the UK carry the delF508 CF mutation on one of the pair of number 7 chromosomes ("carriers").

Presently no effective treatment for CFTR exists and therapy is restricted to combating symptoms. Patients with CF need daily chest physiotherapy, which involves vigorous massage to help loosen the sticky mucus. Patients also need to have any chest infection treated quickly with antibiotics. The usual childhood vaccinations, such as MMR (measles, mumps and rubella) and DTP (diptheria, tetanus and whooping cough) are important for people with CF, and they should also be vaccinated against flu and pneumococcus to help prevent chest infections. With each meal or snack, most people with CF need to take capsules that supply the missing pancreatic enzymes and allow proper digestion. Additional therapy may include daily oral or inhaled antibiotics to counter lung infection, inhaled anti-asthma therapy, corticosteroid tablets, dietary vitamin supplements, especially A and D, inhalation of medication (pulmozyme) to make the sputum less sticky, medicines to relieve constipation or to improve the activity of the enzyme supplements, insulin for CF-related diabetes, medication for CF-associated liver disease, oxygen to help with breathing and help to overcome fertility problems.

The most common CF mutation delF508 results in a mutant protein that is less efficiently folded in the ER, shows a reduced cell surface expression and reduced chloride current capacity. Several therapeutic approaches are considered for CF. One approach is based on gene therapy (introduction of correct CFTR cDNA). Alternatively, boosting of the activity of endogenous mutant CFTR is considered as therapeutic avenue. It is generally considered that a modest increase in chloride conductance of delF508 CFTR would be therapeutic. Investigated are therefore pharmacological improvements of mutant CFTR protein folding in the ER, pharmacological enhancement of cell surface expression of mutant CFTR protein and pharmacological potentiation of chloride conductance by the mutant CFTR protein. Presently, none of these approaches has resulted in an effective drug that corrects the primary problem in CF patients.

Correction of CF will require a correction of the underlying defect, i.e. correction of reduced activity of the chloride channel CFTR in apical membranes of epithelial cells. The majority of CF patients carries a mutant del F508-CFTR protein. The problem to be solved is therefore particularly to increase chloride currents in epithelial cells of patients carrying del F508-CFTR. For efficient therapeutic correction only a partial improvement chloride conductance capacity in these individuals is thought to be sufficient.

SUMMARY OF THE INVENTION

It was found that the CFTR protein is located in glycosphingolipid-rich lipid rafts in the apical membrane of epithelial cells. The activity of the chloride channel CFTR is influenced by its microenvironment which contains glycosphingolipids and ceramide. In view of this it was envisioned that selective local reduction of ceramide will have may a major beneficial stimulatory effect on activity of the chloride channel (delF508)-CFTR and thus constitute a therapeutic avenue for CF. With this in mind it was an object of the present inventors to identify a protein/enzyme that controls the sphingolipid microenvironment of the CFTR protein thereby providing a target for developing a treatment for CF.

The present inventors met this object by discovering an enzyme that is also located in apical membranes of epithelial cells: the non-lysosomal glucosylceramidase. This enzyme catalyzes the conversion of glucosylceramide to ceramide and thus affects the composition of lipid rafts. Identification of the corresponding gene and protein, revealed that it is identical to GBA2 (glucosidase, beta (bile acid) 2) and thus it was found that GBA2 plays an important role in regulation of chloride conductance by CFTR by changing its lipid raft microenvironment.

By identifying as target the non-lysosomal glucosylceramidase it was found that a therapy for CF lies in the, preferably selective, inhibition of GBA2. Inhibition of the enzyme should increase chloride currents and exert a therapeutic effect in patients suffering from CF, particularly those with delF508 CFTR.

The invention thus concerns a method for the treatment of cystic fibrosis, said method comprising the step of administering a therapeutically effective amount of an inhibitor of GBA2 to a subject in need thereof. Or in other words the invention concerns the use of an inhibitor of GBA2 for the preparation of a medicament for the treatment of cystic fibrosis.

Recently a beneficial effect of miglustat (N-butyl-1-deoxynojirimycin) on CF has been reported (Norez et al., FEBS Letters 580 (2006) 2081-2086). In this publication a different mechanism of action, however, has been proposed, viz. the inhibition of endoplasmatic reticulum alpha-glucosidase. Contrary to this publication the present invention allows the generation of compounds that are far more effective and specific therapeutic agents for CF.

DETAILED DESCRIPTION OF THE INVENTION

The non-lysosomal glucosylceramidase is an enzyme that efficiently can convert glucosylceramide to ceramide. To gain insight in the function of the enzyme the present inventors analysed various tissues and cell types for the presence of the non-lysosomal glucosylceramidase. Use was made of a convenient assay: the measurement of hydrolysis of 4-methylumbelliferyl-beta-glucoside in the presence of 5 mM conduritol B-epoxide. Under these conditions degradation of the substrate by the lysosomal glucocerebrosidase (GBA1) is irreversibly inhibited by covalent linkage of conduritol B-epoxide.

The present inventors revealed that the non-lysosomal glucosylceramidase is particularly abundant in epithelial cells and located to their apical membranes. The enrichment of the non-lysosomal glucosylceramidase in isolated apical membranes from epithelial cells is about 450-fold. The non-lysosomal glucosylceramidase is thus located in a similar membrane fraction to the chloride channel CFTR.

The molecular nature of the non-lysosomal gluycosylceramidase was identified after analysis of proteins in apical membrane fractions of cultured epithelial cells. Analysis was performed by two-dimensional gel electrophoresis and protein staining. A candidate 100 kDa protein was identified. The candidate protein was partially digested with trypsin and the amino acid sequence of a tryptic peptide was determined by MS/MS analysis. Comparison of the established amino acid sequence with protein data bases indicated that the GBA2 gene may encode the non-lysosomal glucosylceramidase.

To substantiate that GBA2 truly encodes the non-lysosomal glucosylceramidase we expressed GBA2 cDNA in cells. Analysis of cell lysates revealed that the non-lysosomal glucosylceramidase activity was increased upon expression of GBA2 cDNA. Conversely, expression of GBA2 siRNA led to a reduction in non-lysosomal glucosylceramidase activity. The GBA2 gene product is predicted to be a 100 kDa protein that spans the membrane and its presumed catalytic site is on top of the membrane, see the FIGURE. The following features of GBA2, which is a protein of 972 amino acids (MW 104 kDa) are indicated in the FIGURE: (1) cytosolic domain (aa 706-927) contains di-leucine motive for sorting to PM/endosomes/lysosomes; (2) one transmembrane domain; (3) lumenal domain (aa 1-690) rich in cysteins; (4) predicted catalytic centre on top of lumenal face of membrane.

This structure prediction is entirely consistent with the known features of the enzyme, being membrane bound and degrading glycosphingolipid substrate while inserted in the membrane bilayer.

Following the discovery of GBA2 being responsible for generating ceramide in apical membranes of epithelial cells, the present inventors envisioned that inhibitors of GBA2 should have a beneficial effect in CF. In general beta-glucosidase inhibitors thus should be suitable. In one embodiment of the present invention a beta-glucosidase inhibitor is used for the treatment of CF. In one embodiment the inhibitor according to the present invention comprises an iminosugar moiety. An iminosugar moiety is defined as a structural mimic of a monosaccharide, wherein a nitrogen atom replaces the ring oxygen that is normally present in monosaccharides. In a preferred embodiment the iminosugar comprises a 5- or 6-membered ring wherein at least one nitrogen atom is present. Preferably the remaining 4 or 5 ring atoms are carbon atoms. In one embodiment the inhibitor comprises a monosaccharide having a 6-membered ring wherein one nitrogen atom is present. The iminosugar moiety may have any monosaccharide configuration. Such configuration are known to the carbohydrate chemist. Also the iminosugar encompasses compounds that lack one or more OH groups, e.g. deoxy- or dideoxy-etcetra, from the usual monosaccharide.

It is advantageous to include, e.g. to couple to the beta-glucosidase inhibitor, in particular the iminosugar, a group that allows insertion, or in other words a group that is capable of insertion, in the membrane bilayer. Such a group can also be named a lipophilic group. In case of an iminosugar, such a group may be coupled to any atom of the monosaccharide ring, either directly or conveniently via the oxygen atom of a hydroxyl substituent on a monosaccharide ring atom. In a preferred embodiment a group that is capable of insertion in the membrane bilayer is coupled to a, or the, nitrogen atom in the monosaccharide ring. In order to be capable of inserting in a membrane bilayer, it is preferred that the group coupled to the iminosugar is sufficiently hydrophobic, or in other words lipophilic, to positively interact with the bilayer lipid environment. A group is sufficiently hydrophobic, or lipophilic, if it comprises at least 6 carbon atoms. Preferably the group comprises less than 40 carbon atoms. Thus in one embodiment an iminosugar is substituted with a group comprising 6-40 carbon atoms. Such a group can be considered to be an alkyl chain which may be linear or branched, may be interrupted with one or more heteroatoms such as O, S and N, and also the alkyl chain may contain one or more unsaturations, e.g. double or triple carbon-carbon bonds. For example oleyl chains (C18 with one double, preferably cis, bond) are known to interact well with lipid bilayers. Not counting branching or carbon atom containing substituents on such an alkyl chain, a length corresponding to an alkyl chain of less than 30 carbon atoms or even to 24 or less carbon atoms is usually sufficient for beneficial interaction with membrane bilayers.

Alternatively a group comprising 6-40 carbon atoms can also be regarded as a group comprising a hydrophobic moiety. A suitable description of a hydrophobic moiety is carbon atom containing cyclic group that is capable of inserting in membrane bilayers. Suitably the cyclic group comprises two carbon atom containing rings or preferably even three carbon atom containing rings or more. Advantageously in such a polycyclic structure at least two rings, preferably at least three rings or more preferably all the rings share two or more carbon atoms with another ring. Suitable examples of such groups are cholesterol, β-cholestanol, phenanthrene, adamantane and the like. It is advantageous to couple such a group via a hydroxyl functionality to an alkyl chain which in turn is coupled to an iminosugar, preferably to the ring-nitrogen of the iminosugar. The alkyl chain coupling hydrophobic moiety to iminosugar comprises preferably at least 2, preferably at least 3 carbon atoms. If a large hydrophobic moiety is included in the inhibitor the alkyl chain coupling hydrophobic moiety to iminosugar comprises preferably not more than 12, preferably not more than 10, or 9 or even not more than 8 carbon atoms. The alkyl chain may comprise at least one heteroatom, e.g. an O atom via which the hydrophobic moiety may be coupled to the alkyl chain.

In particular it is known that potent inhibitors of non-lysosomal glucosylceramidase contain a deoxynojirimycin moiety. It is advantageous to include, e.g. to couple to the deoxynojirimycin moiety, a group that allows insertion in the membrane bilayer. A known potent inhibitor of GBA2 is N-[5'-(adamantan-1'-yl-methoxy)-pentan]-1-deoxynojirimycin (AMP-DNM), disclosed in Overkleeft et al., J Biol Chem 1998, vol. 273, no. 41, pp 26522-26527. This structure has an IC50 of about 1 nM for GBA2.

It was found that chloride current upon incubation of delF508-CFTR containing epithelial CF cells with AMP-DNM was restored to such levels that are considered to have a therapeutic effect. Partial restoration of chloride conductance capacity is sufficient to result in major corrections in chloride conductance as also evidenced by improvements in status of mice carrying delF508-CFTR.

Thus inhibition of GBA2 is required for the beneficial effect on the chloride channel delF508-CFTR. AMP-DNM is a potent inhibitor of GBA2 with therapeutic potential. This type of compound can be improved by increasing selectivity. Hydrophobic deoxynojirimycins are also known inhibitors of glucosylceramide synthase. In one embodiment it is considered particularly useful to prevent co-inhibition of glucosylceramide synthase (GCS) as much as possible. More selective compounds can be generated by variation of the sugar configuration and variation of the alkyl chain and/or variation of the hydrophobic moiety and variation of the way in which, or means by which, the hydrophobic group is linked to the sugar moiety, in particular variation in the alkyl chain coupling the hydrophobic moiety and the iminosugar moiety.

In one embodiment an inhibitor according to the invention comprises an iminosugar which is a deoxynojirimycin or derivative thereof. A derivative encompasses deoxynojirimycins with different monosaccharide configurations and/or substituents on monosaccharide OH groups. In one embodiment the deoxynojirimycin is in the glucopyranose configuration, in another embodiment the deoxynojirimycins is in the idopyranose configuration. Suitably the inhibitor is N-[5'-(adamantan-1'-yl-methoxy)-pentan]-1-deoxynojirimycin (AMP-DNM) or N-[5'-(adamantan-1'-yl-methoxy)-pentan]-L-ido-1-deoxynojirimycin (ido-AMP-DNM).

In one embodiment the group comprising 6-40 carbon atoms that is capable of inserting in a membrane bilayer comprises a bulky alkyl group, e.g. a tertiary butyl or neopentyl group. Suitably the neopentyl group results from coupling neopentylalcohol. Advantageously the tertiary butyl or neopentyl group is at the terminal position of the group having 6-40 carbon atoms, in particular the alkyl chain, that is capable of inserting in a membrane bilayer. A suitable inhibitor according to the invention is N-[5'-neopentyloxy-pentan]-1-deoxynojirimycin or N-[5'-neopentyloxy-pentan]-L-ido-1-deoxynojirimycin. Other suitable inhibitors are similar compounds like N-[5'-neopentyloxy-pentan]-1-deoxynojirimycin but wherein the pentane alkyl chain comprises less or more carbon atoms, in particular $CH_2$ groups, e.g. N-[5'-neopentyloxy-butan]-, -hexan]-, -heptan]-, -octan]-, -nonan]-, -decan]-1-deoxynojirimycin etc., or the L-ido compounds.

In a preferred embodiment the inhibitor according to the present invention has an IC50 for GBA2 of less than 250 nM, preferably less than 150 nm. In another embodiment it is preferred the inhibitor has an IC50 for GCS of more than 1 mM, preferably more than 100 μM.

The invention also concerns N-[5'-neopentyloxy-alkyl]-1-deoxynojirimycin or N-[5'-neopentyloxy-alkyl]-L-ido-1-deoxynojirimycin, wherein alkyl means an alkylene group having 4-12 carbon atoms, preferably 4-11, 4-10, 4-9, 4-8, 4-7 carbon atoms, preferably having 4-12 $CH_2$ groups, preferably 4-11, 4-10, 4-9, 4-8, 4-7 $CH_2$ groups in a straight chain. The invention also concerns the use of such compounds as a pharmaceutical and pharmaceutical com[positions comprising such a compound with a pharmaceutically acceptable carrier.

Importantly, the positive effects of the inhibitors according to the present invention can not be ascribed to improved ER folding of delF508-CFTR by inhibition of ER alpha-glucosidase or inhibition of glycosphingolipid synthesis. The present invention presents thus an entirely novel insight, i.e. that specific inhibitors of GBA2 are highly specific therapeutic agents for treatment of cystic fibrosis.

EXAMPLES

The effects of AMP-DNM on cAMP-activated chloride current in delF508-CFTR containing epithelial CF cells were studied with the following assay:

Perforated whole-cell patch-clamp analysis was applied to CF15 cells (human nasal epithelial cell line obtained from delF508 homozygous patient). Patch electrodes (GC150-TF10, Harvard Apparatus, USA) filled with intracellular solution (resistances of 3-4 MΩ) were connected to the RK-400 amplifier (Biologic, France) through an Ag/AgCl pellet. External solution (mM): 145 NaCl, 4 CsCl, 1 $MgCl_2$, 1 $CaCl_2$, 5 d-glucose, 10 TES (pH 7.4, 315 mOsm). Intra-pipette solution (mM): 113 l-aspartic acid, 113 CsOH, 27 CsCl, 1 NaCl, 1 EGTA, 1 $MgCl_2$, 3 Mg-ATP (ex-temporane), 10 TES (pH 7.2 with CsOH, 285 mOsm) and amphotericin B (100 μg/ml) renewed every 2 h. Only cells with input resistance 15 MΩ were analysed. The mean access resistance and whole cell capacitance were 12±0.6 MΩ and 35±4.3 pF (n=44). Currents were obtained in response to voltage steps from −80 to +80 mV in 20 mV increment. Data were collected using pClamp 6.0.3 package software (Axon Instruments, USA). CFTR Cl⁻ channel activity was assayed on a cell population by the iodide ($^{125}I$) efflux technique.

It was found that incubation of epithelial cells with 10 nM AMP-DNM restores cAMP-activated chloride current in del F508-CFTR containing epithelial CF cells up to 30% of normal levels. Such degree of correction is considered to be sufficient for a therapeutic effect.

To test the therapeutic potential of GBA2 inhibitors for CF further the effects of AMP-DNM on intestine explants from ileal mucosa of delF508 mice were analysed. The following assay was used:

Rotterdam delF508/delF508-CFTR mice ($Cfr^{tm1\ Eur}$), their littermate controls (FVB inbred, 14-17 weeks old, weight between 20 and 30 g, kept on solid food in a pathogen-free environment) and Cftr-KO mice ($Cftr^{tm2\ Cam}$) were used. Muscle-stripped ileal mucosa was incubated in William's E-Glutamax medium supplemented with insulin (10 μg/ml) and dexamethasone (20 μg/ml). At different time points, the compound was removed by repeated washings followed by short-circuit current (Isc) measurements in mini-Ussing chambers. Western blotting was as performed and immuno-blots were probed with monoclonal mouse anti-CFTR antibody (10 μg/ml, $IgG_1$ M3A7, Chemicon, USA). The protein levels were expressed as densitometry and percentage of controls. For immunohistochemistry, tissues were fixed in 4% (wt/vol) paraformaldehyde. Sections (5 μm) were stained with the antibody R3195 (1:500).

It was observed that 10 nM AMP-DNM rescues a mature and functional delF508-CFTR in the intestinal crypts of ileal mucosa from delF508 mice.

It was noted that there is a tight relation between inhibitory capacity of compounds towards GBA2 (measured by analysis of hydrolysis of 4-methylumbelliferyl-beta glucoside in the presence of excess conduritol B-epoxide by GBA2 containing membranes) and positive effects on chloride current.

To test further the structural requirements compounds varying in spacer and hydrophobic group were examined (see table 1). Again it was noticed that inhibitory capacity of GBA2 predicted well correction of chloride current.

TABLE 1

Variation in group that is capable of insertion in membrane bilayer
Structures of tested iminosugars with respect to ability to improve chloride current and
their IC50 values for GBA2 and GCS as determined in specific assays.

| | | GBA2 | GCS |
|---|---|---|---|
| N-[5'-(adamantan-1'-yl-methoxy)-pentan]-1-deoxynojirimycin | IC50 | 1 nM | 0.2 μM |
| N-nonyl-1-deoxynojirimycin | IC50 | 6 nM | 8 μM |
| N-[5'-neopentyloxy-pentan]-1-deoxynojirimycin | IC50 | 30 nM | >100 μM |
| N-[6'-adamantyl-hexan]-1-deoxynojirimycin | IC50 | 1 nM | 7.5 μM |
| N-[5'-(adamantan-1'-yl-methoxy)-butan]-1-deoxynojirimycin | IC50 | 2 nM | 10 μM |

TABLE 1-continued

Variation in group that is capable of insertion in membrane bilayer
Structures of tested iminosugars with respect to ability to improve chloride current and
their IC50 values for GBA2 and GCS as determined in specific assays.

| | | GBA2 | GCS |
|---|---|---|---|
| Comparative example | | | |

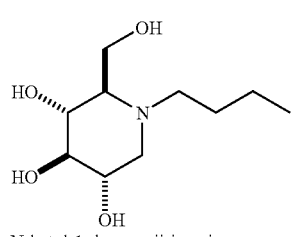

N-butyl-1-deoxynojirimycin

IC50   300 nM   80 μM

To increase specificity of inhibition GBA2 in comparison to GCS, a butanoyl-spacer or hexyl-spacer is found to be advantageous. The hydrophobic group may also be varied. An example in this connection is N-[5'-neopentyloxy-pentan]-1-deoxynojirimycin. Albeit its IC50 for GBA2 is poorer compared to AMP-DNM, it is a relatively more specific inhibitor since it hardly inhibits GCS.

Determination OF IC50 Values

IC50 values of non-lysosomal glucosylceramidase and glucosylceramide synthase (GCS) were determined by exposing enzyme preparations to various dilutions of inhibitors and determining the concentration at which enzyme activity was reduced by 50%. Assays were carried out as described in J. Biol. Chem, 273, 26522-27 (1998) on page 26523 under the heading enzyme assays.

Synthesis Scheme of Deoxynojirimycin Compounds

The synthesis of various suitable deoxynojirimycin based inhibitors is well described elsewhere, e.g., J. Biol. Chem, 1998, vol 273, pp 26522-27 and U.S. Pat. No. 6,177,447. Herebelow a scheme is presented for the synthesis of N-[5'-neopentyloxy-pentan]-1-deoxynojirimycin. All steps are standard for the organic chemist, and appropriate reaction conditions can be routinely established.

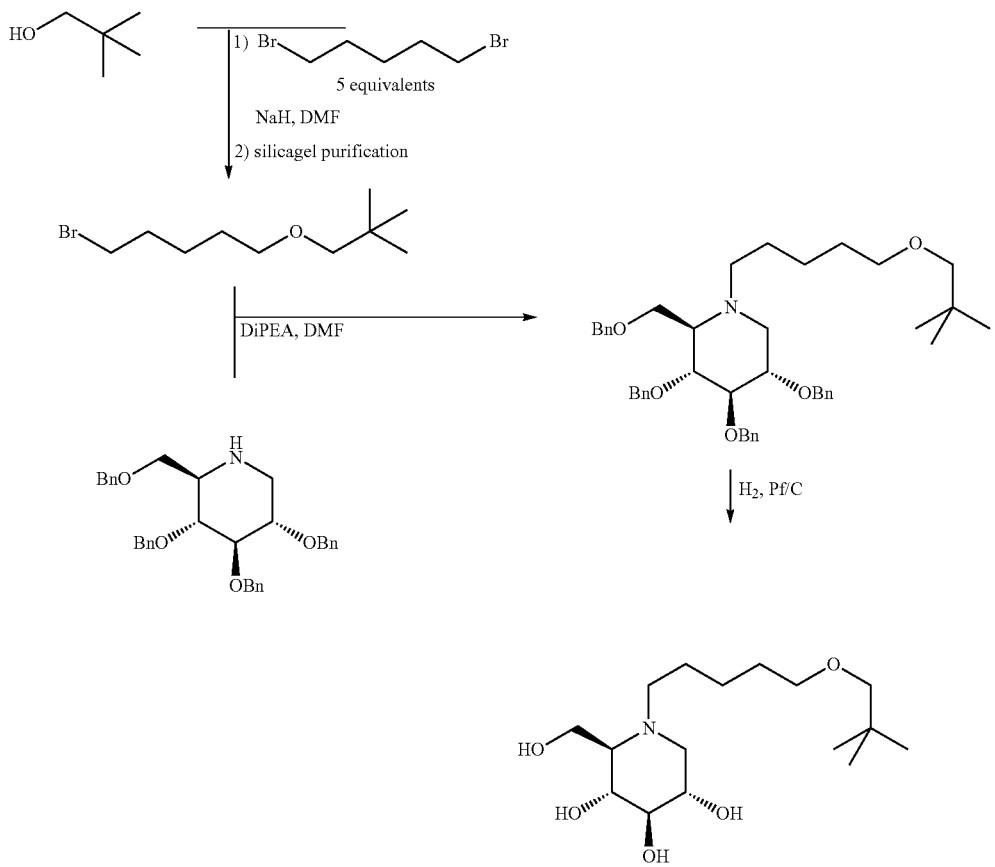

The invention claimed is:

1. A method for treating a subject with cystic fibrosis, comprising administering to a subject in need thereof an effective amount of an inhibitor of glucosidase, beta (bile acid) 2 (GBA2) that comprises:
   (a) a deoxynojirimycin moiety, or a derivative thereof, coupled to
   (b) a 6-40 carbon atom group that inserts into a membrane bilayer, wherein the carbon atom group comprises a hydrophobic moiety which comprises three or more organic ring structures wherein a ring shares two or more carbon atoms with another ring.

2. The method according to claim 1, wherein the carbon atom group is bonded to the nitrogen atom of said deoxynojirimycin moiety.

3. The method according to claim 1, wherein said deoxynojirimycin is in a glucopyranose configuration.

4. The method according to claim 1, wherein said deoxynojirimycin is in a idopyranose configuration.

5. The method according to claim 1, wherein the hydrophobic moiety is cholesterol, β-cholestanol, phenanthrene or adamantane.

6. The method according to claim 1, wherein the inhibitor is selected from the group consisting of
   (a) N-[5'-(adamantan-1'-yl-methoxy)-pentan]-1-deoxynojirimycin, and
   (b) N-[5'-(adamantan-1'-yl-methoxy)-pentan]-L-ido-1-deoxynojirimycin.

7. The method according to claim 2, wherein said deoxynojirimycin is in a glucopyranose configuration.

8. The method according to claim 2, wherein said deoxynojirimycin is in a idopyranose configuration.

9. The method according to claim 2, wherein the hydrophobic moiety is cholesterol, β-cholestanol, phenanthrene or adamantane.

10. The method according to claim 3, wherein the hydrophobic moiety is cholesterol, β-cholestanol, phenanthrene or adamantane.

11. The method according to claim 4, wherein the hydrophobic moiety is cholesterol, β-cholestanol, phenanthrene or adamantane.

* * * * *

UNITED STATES PATENT AND TRADEMARK OFFICE
CERTIFICATE OF CORRECTION

PATENT NO. : 8,410,081 B2  Page 1 of 1
APPLICATION NO. : 12/298506
DATED : April 2, 2013
INVENTOR(S) : Aerts et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this
First Day of September, 2015

Michelle K. Lee
*Director of the United States Patent and Trademark Office*